United States Patent
Cornwall et al.

(10) Patent No.: US 11,013,611 B2
(45) Date of Patent: May 25, 2021

(54) SYSTEMS AND METHODS FOR TREATING SPINAL DEFORMITIES

(71) Applicant: NuVasive, inc., San Diego, CA (US)

(72) Inventors: G. Bryan Cornwall, San Diego, CA (US); Jonathan Spangler, Del Mar, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 16/228,703

(22) Filed: Dec. 20, 2018

(65) Prior Publication Data

US 2019/0201211 A1   Jul. 4, 2019

Related U.S. Application Data

(63) Continuation of application No. 15/421,679, filed on Feb. 1, 2017, now Pat. No. 10,195,047, which is a continuation of application No. 14/183,198, filed on Feb. 18, 2014, now Pat. No. 9,566,090, which is a continuation of application No. 13/438,828, filed on Apr. 3, 2012, now Pat. No. 8,652,177, which is a
(Continued)

(51) Int. Cl.
| | | |
|---|---|---|
| *A61B 17/88* | (2006.01) | |
| *A61F 2/44* | (2006.01) | |
| *A61B 17/70* | (2006.01) | |
| *A61F 2/30* | (2006.01) | |

(52) U.S. Cl.
CPC ........ *A61F 2/4455* (2013.01); *A61B 17/7001* (2013.01); *A61B 17/7005* (2013.01); *A61B 17/7022* (2013.01); *A61B 17/7032* (2013.01); *A61F 2/447* (2013.01); *A61B 17/7007* (2013.01); *A61F 2002/30774* (2013.01); *A61F 2002/30828* (2013.01); *A61F 2002/30904* (2013.01)

(58) Field of Classification Search
CPC ................... A61F 2/4455; A61F 2/447; A61F 2002/30774; A61F 2002/30828; A61F 2002/30904; A61B 17/7001; A61B 17/7005; A61B 17/7022; A61B 17/7032; A61B 17/7007
USPC .............. 606/265, 266, 270, 279; 623/17.11, 623/17.16
See application file for complete search history.

(56) References Cited

U.S. PATENT DOCUMENTS

| | | |
|---|---|---|
| 3,426,364 A | 2/1969 | Lumb |
| 4,667,664 A | 5/1987 | Taylor |

(Continued)

FOREIGN PATENT DOCUMENTS

| | | |
|---|---|---|
| CA | 2015507 | 5/1999 |
| EP | 0369603 | 5/1990 |

(Continued)

*Primary Examiner* — Ellen C Hammond
*Assistant Examiner* — David C Comstock
(74) *Attorney, Agent, or Firm* — NuVasive, Inc.

(57) ABSTRACT

Systems and methods of treating spinal deformity, including one or more intervertebral implants to be introduced laterally into respective intervertebral spaces, a plurality of bone screws introduced generally laterally into vertebral bodies adjacent to the intervertebral implants and/or the intervertebral implants themselves, and a cable dimensioned to be coupled to the bone screws and manipulated to adjust and/or correct the spinal deformity.

20 Claims, 8 Drawing Sheets

Related U.S. Application Data continuation of application No. 11/490,995, filed on Jul. 20, 2006, now Pat. No. 8,147,521.

(60) Provisional application No. 60/701,308, filed on Jul. 20, 2005.

(56) References Cited

U.S. PATENT DOCUMENTS

| | | | |
|---|---|---|---|
| 4,743,256 A | 5/1988 | Brantigan |
| 4,834,757 A | 5/1989 | Brantigan |
| 4,877,020 A | 10/1989 | Vich |
| 4,878,915 A | 11/1989 | Brantigan |
| 4,950,296 A | 8/1990 | Mcintyre |
| 4,961,740 A | 10/1990 | Ray |
| 5,026,373 A | 6/1991 | Ray |
| 5,055,104 A | 10/1991 | Ray |
| 5,171,278 A | 12/1992 | Pisharodi |
| 5,192,327 A | 3/1993 | Brantigan |
| 5,254,118 A | 10/1993 | Mirkovic |
| 5,304,210 A | 4/1994 | Crook |
| 5,306,307 A | 4/1994 | Senter |
| 5,306,309 A | 4/1994 | Wagner |
| 5,334,204 A | 8/1994 | Clewett |
| 5,397,364 A | 3/1995 | Kozak |
| 5,425,772 A | 6/1995 | Brantigan |
| 5,443,514 A | 8/1995 | Steffee |
| 5,458,638 A | 10/1995 | Kuslich |
| 5,484,437 A | 1/1996 | Michelson |
| 5,489,308 A | 2/1996 | Kuslich |
| 5,514,180 A | 5/1996 | Heggeness |
| 5,522,899 A | 6/1996 | Michelson |
| 5,593,409 A | 1/1997 | Michelson |
| 5,607,424 A | 3/1997 | Tropiano |
| 5,609,636 A | 3/1997 | Kohrs |
| 5,645,598 A | 7/1997 | Brosnahan |
| 5,653,761 A | 8/1997 | Pisharodi |
| 5,653,762 A | 8/1997 | Pisharodi |
| 5,658,336 A | 8/1997 | Pisharodi |
| 5,658,337 A | 8/1997 | Kohrs |
| 5,662,710 A | 9/1997 | Bonutti |
| 5,665,122 A | 9/1997 | Kambin |
| 5,669,909 A | 9/1997 | Zdeblick |
| 5,683,391 A | 11/1997 | Boyd |
| 5,683,394 A | 11/1997 | Rinner |
| 5,683,464 A | 11/1997 | Wagner |
| 5,700,291 A | 12/1997 | Kuslich |
| 5,702,449 A | 12/1997 | Mckay |
| 5,716,415 A | 2/1998 | Steffee |
| 5,720,748 A | 2/1998 | Kuslich |
| 5,728,159 A | 3/1998 | Stroever |
| 5,741,253 A | 4/1998 | Michelson |
| 5,766,252 A | 6/1998 | Henry |
| 5,772,661 A | 6/1998 | Michelson |
| 5,782,830 A | 7/1998 | Farris |
| 5,782,919 A | 7/1998 | Zdeblick |
| 5,785,710 A | 7/1998 | Michelson |
| 5,797,917 A | 8/1998 | Boyd |
| 5,814,084 A | 9/1998 | Grivas |
| 5,860,973 A | 1/1999 | Michelson |
| 5,865,845 A | 2/1999 | Thalgott |
| 5,865,846 A | 2/1999 | Bryan |
| 5,865,848 A | 2/1999 | Baker |
| 5,885,299 A | 3/1999 | Winslow |
| 5,888,224 A | 3/1999 | Beckers |
| 5,893,890 A | 4/1999 | Pisharodi |
| 5,904,719 A | 5/1999 | Errico |
| 5,968,098 A | 10/1999 | Winslow |
| 5,984,923 A * | 11/1999 | Breard ............... A61B 17/7002 606/259 |
| 6,004,326 A | 12/1999 | Castro |
| 6,033,405 A | 3/2000 | Winslow |
| 6,045,580 A | 4/2000 | Scarborough |
| 6,059,829 A | 5/2000 | Schläpfer |
| 6,063,088 A | 5/2000 | Winslow |
| 6,066,175 A | 5/2000 | Henderson |
| 6,080,158 A | 6/2000 | Lin |
| 6,083,225 A | 7/2000 | Winslow |
| 6,096,080 A | 8/2000 | Nicholson |
| 6,102,948 A | 8/2000 | Brosnahan |
| 6,106,557 A | 8/2000 | Robioneck |
| 6,120,503 A | 9/2000 | Michelson |
| 6,120,506 A | 9/2000 | Kohrs |
| 6,143,033 A | 11/2000 | Paul |
| 6,156,037 A | 12/2000 | Lehuec |
| 6,159,211 A | 12/2000 | Boriani |
| 6,159,245 A | 12/2000 | Meriwether |
| 6,176,882 B1 | 1/2001 | Biedermann |
| 6,200,347 B1 | 3/2001 | Anderson |
| 6,206,922 B1 | 3/2001 | Zdeblick |
| 6,224,607 B1 | 5/2001 | Michelson |
| 6,224,631 B1 | 5/2001 | Kohrs |
| 6,241,771 B1 | 6/2001 | Gresser |
| 6,251,140 B1 | 6/2001 | Marino |
| 6,258,125 B1 | 7/2001 | Paul |
| 6,277,149 B1 | 8/2001 | Boyle |
| 6,296,647 B1 | 10/2001 | Robioneck |
| 6,306,170 B2 | 10/2001 | Ray |
| RE37,479 E | 12/2001 | Kuslich |
| 6,325,827 B1 | 12/2001 | Lin |
| 6,371,989 B1 | 4/2002 | Chauvin |
| 6,383,221 B1 | 5/2002 | Scarborough |
| 6,409,766 B1 | 6/2002 | Brett |
| 6,432,140 B1 | 8/2002 | Lin |
| 6,447,547 B1 | 9/2002 | Michelson |
| 6,468,311 B2 | 10/2002 | Boyd |
| 6,491,724 B1 | 12/2002 | Ferree |
| 6,527,773 B1 | 3/2003 | Lin |
| D472,634 S | 4/2003 | Anderson |
| D473,650 S | 4/2003 | Anderson |
| 6,547,823 B2 | 4/2003 | Scarborough |
| 6,635,086 B2 | 10/2003 | Lin |
| 6,648,895 B2 | 11/2003 | Burkus |
| 6,676,703 B2 | 1/2004 | Biscup |
| 6,695,845 B2 | 2/2004 | Dixon |
| 6,695,851 B2 | 2/2004 | Zdeblick |
| 6,702,823 B2 | 3/2004 | Iaia |
| 6,743,255 B2 | 6/2004 | Ferree |
| 6,746,484 B1 | 6/2004 | Liu |
| 6,824,564 B2 | 11/2004 | Crozet |
| D503,801 S | 4/2005 | Jackson |
| 6,899,714 B2 | 5/2005 | Vaughan |
| 6,942,698 B1 | 9/2005 | Jackson |
| 6,964,687 B1 | 11/2005 | Bernard |
| 6,979,353 B2 | 12/2005 | Bresina |
| 6,984,245 B2 | 1/2006 | Mcgahan |
| 6,986,788 B2 | 1/2006 | Paul |
| 6,989,031 B2 | 1/2006 | Michelson |
| 7,018,416 B2 | 3/2006 | Hanson |
| D530,423 S | 10/2006 | Miles |
| D594,986 S | 6/2009 | Miles et al. |
| 7,686,833 B1 * | 3/2010 | Muhanna ............ A61B 17/7032 606/257 |
| 2001/0025180 A1 | 9/2001 | Jackson |
| 2002/0055738 A1 | 5/2002 | Lieberman |
| 2002/0107572 A1 | 8/2002 | Foley |
| 2002/0116065 A1 | 8/2002 | Jackson |
| 2002/0138146 A1 | 9/2002 | Jackson |
| 2002/0161368 A1 * | 10/2002 | Foley ............... A61B 17/00234 128/898 |
| 2003/0088251 A1 | 5/2003 | Braun |
| 2003/0105528 A1 | 6/2003 | Shimp |
| 2003/0109928 A1 | 6/2003 | Pasquet |
| 2003/0125739 A1 | 7/2003 | Bagga |
| 2003/0139812 A1 | 7/2003 | Garcia |
| 2004/0034353 A1 | 2/2004 | Michelson |
| 2004/0122424 A1 | 6/2004 | Ferree |
| 2004/0215190 A1 * | 10/2004 | Nguyen ............ A61B 17/7001 606/86 A |
| 2004/0249379 A1 | 12/2004 | Winslow |
| 2005/0033295 A1 * | 2/2005 | Wisnewski ........ A61B 17/7011 606/250 |
| 2005/0033432 A1 | 2/2005 | Gordon |
| 2005/0071008 A1 | 3/2005 | Kirschman |

(56) References Cited

U.S. PATENT DOCUMENTS

| | | | |
|---|---|---|---|
| 2005/0085815 A1* | 4/2005 | Harms | A61B 17/645 606/279 |
| 2005/0101960 A1 | 5/2005 | Fiere | |
| 2005/0131405 A1* | 6/2005 | Molz, IV | A61B 17/7013 606/247 |
| 2005/0159813 A1 | 7/2005 | Molz | |
| 2005/0203538 A1 | 9/2005 | Lo | |
| 2005/0209698 A1* | 9/2005 | Gordon | A61B 17/7023 623/17.15 |
| 2005/0228501 A1 | 10/2005 | Miller | |
| 2005/0256578 A1 | 11/2005 | Blatt | |
| 2005/0277922 A1* | 12/2005 | Trieu | A61B 17/7031 606/257 |
| 2006/0036243 A1 | 2/2006 | Sasso | |
| 2006/0074490 A1 | 4/2006 | Sweeney | |
| 2006/0217807 A1 | 9/2006 | Peterman | |
| 2007/0016200 A1* | 1/2007 | Jackson | A61B 17/7082 623/17.16 |
| 2007/0073293 A1* | 3/2007 | Martz | A61B 17/0401 606/86 A |

FOREIGN PATENT DOCUMENTS

| | | |
|---|---|---|
| EP | 0716840 | 6/1996 |
| EP | 0784967 | 7/1997 |
| EP | 0796593 | 9/1997 |
| EP | 0880938 | 12/1998 |
| EP | 1188424 A1 | 3/2002 |
| GB | 2294399 | 5/1996 |
| WO | WO-1991006261 | 5/1991 |
| WO | WO-1996008205 | 3/1996 |
| WO | WO-1997033525 | 9/1997 |
| WO | WO-1997037620 | 10/1997 |
| WO | WO-1998009586 | 3/1998 |
| WO | WO-1998017208 | 4/1998 |
| WO | WO-1999008627 | 2/1999 |
| WO | WO-1999038461 | 8/1999 |

* cited by examiner

SYSTEMS AND METHODS FOR TREATING SPINAL DEFORMITIES

CROSS-REFERENCES TO RELATED APPLICATIONS

This application is a continuation of U.S. patent application Ser. No. 15/421,679 filed Feb. 1, 2017, which is a continuation of U.S. patent application Ser. No. 14/183,198 filed Feb. 18, 2014 (now U.S. Pat. No. 9,566,090), which is a continuation of U.S. patent application Ser. No. 13/438,828 filed Apr. 3, 2012 (now U.S. Pat. No. 8,652,177), which is a continuation of U.S. patent application Ser. No. 11/490,995 filed Jul. 20, 2006 (now U.S. Pat. No. 8,147,521), which claims the benefit of priority from U.S. Provisional Application Ser. No. 60/701,308, filed on Jul. 20, 2005, the entire contents of which are hereby expressly incorporated by reference into this disclosure as if set forth fully herein.

BACKGROUND OF THE INVENTION

I. Field of the Invention

The present invention relates generally to surgical fixation and, more particularly, to systems and methods for treating spinal deformities.

II. Discussion of the Prior Art

The human spine exhibits some degree of curvature at different levels to facilitate normal physiologic function. Correction of the spine may be required when the curvature of the spine deviates substantially from normal. The misalignment usually manifests itself in an asymmetry of the vertebral bodies, such that, over a sequence of vertebrae, the spine twists and/or bends to one side. This lateral deviation of the spine is commonly termed scoliosis.

Spinal deformity occurs when a patient has abnormal frontal or sagittal plane alignment. At the same time, the cervical and lumbar spine exhibit lordosis, while the thoracic spine has kyphosis. Thus, when performing spinal fusion, surgeons may be required to preserve or restore both front plane and sagittal alignment while taking lordosis and kyphosis into account. Scoliosis can develop later in life, as joints in the spine degenerate and create a bend in the back which may require surgery.

Surgery has traditionally involved procedures such as the Harrington, Dwyer and Zielke, and Luque procedures which rely on implanted rods, laminar/pedicle hooks, and screws to maintain the correction until stabilized by fusion of vertebrae. According to these surgical techniques, treating scoliosis includes the implantation of a plurality of hooks and/or screws into the spinal bones, connecting rods to these elements, physically bracing the bones into the desired positions, and permitting the bones to fuse across the entire assembly. This immobilization often requires anterior plates, rods and screws and posterior rods, hooks and/or screws. Alternatively, spacer elements are positioned between the sequential bones, which spacers are often designed to permit fusion of the bone into the matrix of the spacer from either end, hastening the necessary rigidity of the developing bone structure.

The Harrington instrumentation system has been used successfully for some time, but because the distraction rod is fixed to the spine in only two places, failure at either end causes the entire system to fail. Another deficiency with existing mechanisms and approaches is that the single rod used to correct the defects must be contoured to fit various attachment sites. In patients having compound spinal deformity, this may be extremely difficult. A further problem is that the contoured rod frequently limits further correction of certain types of deformities. That is, once the rod is in position, further correction of the deformity is difficult, since existing systems tend to limit incremental alignment procedures.

The present invention is directed at overcoming, or at least improving upon, the disadvantages of the prior art.

SUMMARY OF THE INVENTION

The present invention accomplishes this goal by providing a spinal alignment system that may be affixed to a plurality of vertebra via any number of suitable techniques, such as open surgery or minimally invasive surgery. The spinal alignment system can take the form of either a single level system or a multi-level system. Fixing adjacent vertebra in this manner is advantageous in that it provides a desired level of flexibility to parts of the spine, while also providing long-term durability and consistent stabilization.

According to one broad aspect of the present invention, a single level spinal alignment system includes a cable, a superior bone screw, an inferior bone screw, and at least one spinal fusion implant. This single level spinal alignment system may be used to treat spinal deformities, including but not limited to scoliosis. To do so, access may be provided through a lateral approach utilizing either an open or a minimally invasive technique. According to one aspect of the present invention, a spinal fusion implant is introduced into a targeted intervertebral space after access has been achieved. A superior bone screw and an inferior bone screw may thereafter be anchored into the immediately superior and immediately inferior vertebral bodies, respectively, on either side of the targeted intervertebral space. According to one embodiment, the cable may be locked to the superior bone screw and thereafter pulled or otherwise manipulated such that the distance between the superior bone screw and inferior bone screw is reduced. This serves to move the superior and inferior vertebral bodies so as to correct or minimize the spinal deformity. After this reduction, the cable may be locked to the inferior bone screw to maintain the superior and inferior vertebral bodies in the resulting configuration. In addition to manner described above, it is also contemplated that the cable may be coupled to the superior bone screw prior to introducing the inferior bone screw.

According to one broad aspect of the present invention, a multi level spinal alignment system comprises a cable, a superior bone screw, an inferior bone screw, at least one middle bone screw, and at least one spinal fusion implant. The multi level spinal alignment system of the present invention may be used to treat spinal deformities, including but not limited to scoliosis. To do so, access may be provided through a lateral approach utilizing either an open or minimally invasive technique. According to one aspect of the present invention, a plurality of spinal fusion implants are introduced into targeted intervertebral spaces after access has been achieved. A superior bone screw is introduced into the vertebral body immediately superior to the highest of the spinal fusion implants. An inferior bone screw is introduced into the vertebral body immediately inferior to the lowest of the spinal fusion implants. A middle bone screw is introduced into each vertebral body in between the superior bone screw and the inferior bone screw.

According to one embodiment, the cable may be threaded or otherwise passed through apertures in the middle screws, and thereafter locked to the superior bone screw. The cable may then be pulled or otherwise manipulated such that the distance between the superior bone screw, the inferior bone screw, and any middle bone screws is reduced. This serves to move the superior vertebral body, the inferior vertebral body, and any intermediate vertebral bodies so as to correct or minimize the spinal deformity. After this reduction, the cable may be locked to the middle bone screws and inferior bone screw to maintain the superior vertebral body, inferior vertebral body, and any intermediate vertebral bodies in the resulting configuration. In addition to manner described above, it is also contemplated that the cable may be coupled to one of the bone screws (e.g. the superior bone screw) prior to introducing the other bone screws (e.g. the inferior bone screw).

The cable is an elongated flexible member with a first end, a second end, a head member located at the first end, and a main portion extending from the head member to the second end. The head member of the cable is preferably located at one end of the cable. The head member may be a spherical body shaped to be relieved within and locked into the superior bone screw. The head member may also be dimensioned in any number of suitable shapes necessary to facilitate surgical fixation, including but not limited to oval, flat or rectangular. The head member may also include an aperture extending generally perpendicularly through the surface of the head member to accept a post or other purchase element provided on the superior bone screw.

The main portion may be composed of any substantially and suitable flexible material capable of performing spinal alignment including, but not limited to, steel, nylon, plastics, or various composites. Accordingly, any suitable shape for the cable is useable, whether cylindrical, flat, square, or other suitable shapes and configurations within the scope of the present invention. The main portion of the cable may also include a plurality of apertures located near the proximal or second end of the cable whereby the apertures extend generally perpendicularly through the surface of the cable. As is described in detail below, the cable is used to straighten curvature in the spine.

The superior bone screw may either be fixed-angle or polyaxial. Fixed-angle screws and polyaxial screws are generally known in the art and will not be further explained herein. Other fasteners or anchors may also be used, such as those commonly used in surgical fixation procedures. The superior bone screw may be cannulated in order to allow precise insertion with the use of a K-wire or other surgical insertion-facilitating device that may be commonly used in such a procedure. The superior bone screw may include a receiving post instead of the usual receiving head on a fixed and polyaxial screw.

The inferior bone screw may either be fixed-angle or polyaxial. Other fasteners or anchors may be used, such that is commonly used in surgical fixation procedures. The inferior bone screw may be cannulated in order to allow precise insertion with the use of a K-wire or other surgical insertion-facilitating device that may be commonly used in such a procedure. The inferior bone screw may include a receiving post instead of the usual receiving head on a fixed and polyaxial screw.

The middle bone screw(s) may be either fixed-angle or polyaxial. It should also be noted that the middle bone screw(s) may include an aperture located on the head of the screw. Each aperture has a substantially spherical inside surface with a top diameter and a bottom diameter with a circular shape. It should be noted that any combination of fixed and/or polyaxial screws may be used in connection with the superior bone screw, the inferior bone screw, and/or the middle bone screw(s).

The spinal fusion implants are of non-bone construction and may be provided in any number of suitable shapes and sizes depending upon the particular surgical need. The spinal fusion implant may be dimensioned for use in the cervical and/or lumbar spine in any variety of ways, such as the design described in commonly owned and co-pending U.S. patent application Ser. No. 11/093,409, the entire contents of which are hereby expressly incorporated by reference into this disclosure as if set forth fully herein.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal alignment system disclosed herein boasts a variety of inventive features and components that warrant patent protection, both individually and in combination.

Figure 1:
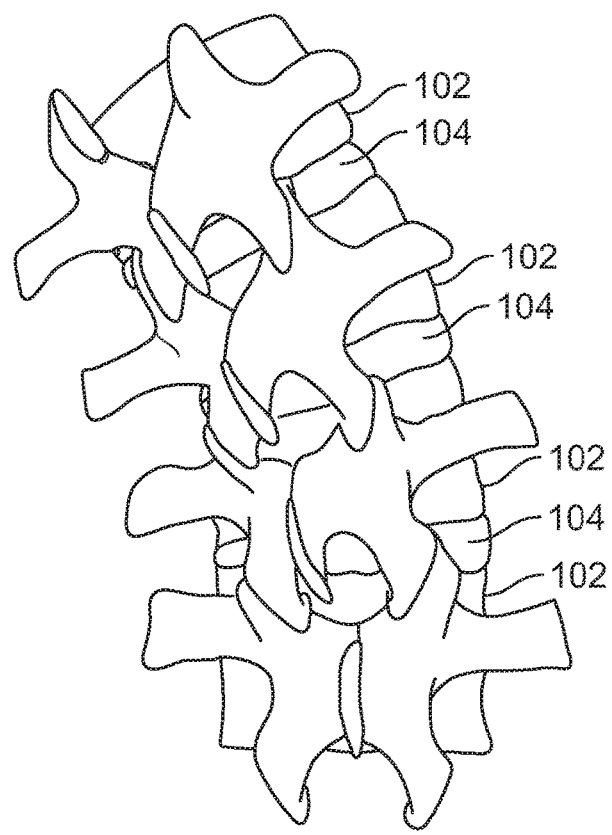
FIG. 1 is a front view of a human spine having scoliosis.

FIG. 1 shows a human spine (comprising vertebrae 102 and intervertebral discs 104) with scoliosis, which is in need of correction according to the present invention. As will be described in detail below, the present invention accomplishes this by providing a spinal alignment system comprising one or more spinal fusion implants, a plurality of bone screws, and a cable which cooperate to correct or minimize the particular spinal deformity. The spinal alignment system can take the form of either a single level system or a multi-level system. Fixing adjacent vertebra in this manner is advantageous in that it provides a desired level of flexibility to parts of the spine, while also providing long-term durability and consistent stabilization.

Figure 2:
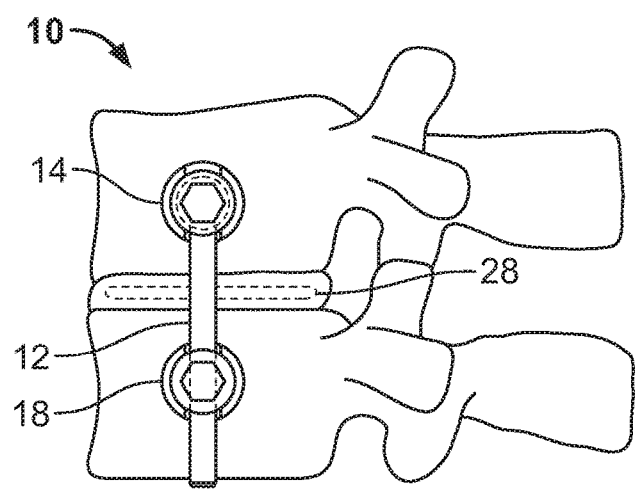
FIG. 2 is a lateral view of a single level spinal alignment system according to a first embodiment of the present invention.
Figure 3:
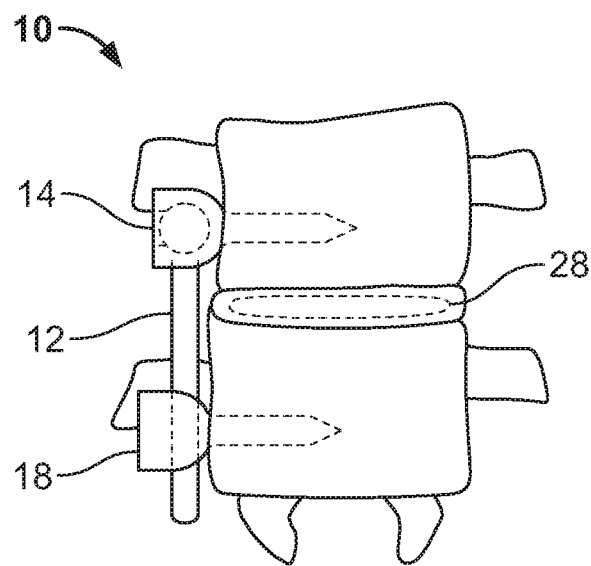
FIG. 3 is an anterior view of the single level spinal alignment system according to the embodiment drawn in FIG. 2.

FIGS. 2-3 are lateral and anterior views (respectively) of a single level spinal alignment system 10 according to a first broad aspect of the present invention. The spinal alignment system 10 includes a cable 12, a superior bone screw 14, an inferior bone screw 18, and at least one spinal fusion implant 28, all of which may be preferably introduced into the patient in a generally lateral direction (via open or minimally invasive techniques). According to one aspect of the present invention, a spinal fusion implant 28 is introduced into a targeted intervertebral space after access has been achieved. A superior bone screw 14 and an inferior bone screw 18 may thereafter be anchored into the immediately superior and immediately inferior vertebral bodies, respectively, on either side of the targeted intervertebral space. As will be appreciated, one or more of the bone screws 14, 18 may be implanted prior to the implant 28 without departing from the scope of the present invention. According to one embodiment, the cable 12 may be locked to the superior bone screw 14 and thereafter pulled or otherwise manipulated such that the distance between the superior bone screw 14 and inferior bone screw 18 is reduced. This serves to move the superior and inferior vertebral bodies so as to correct or minimize the spinal deformity. After this reduction, the cable 12 may be locked to the inferior bone screw 18 to maintain the superior and inferior vertebral bodies in the resulting configuration. In addition to manner described above, it is also contemplated that the cable 12 may be coupled to the superior bone screw 14 prior to introducing the inferior bone screw 18, and that the cable 12 may be coupled to the inferior bone screw 18 before the superior bone screw 14.

Figure 4:
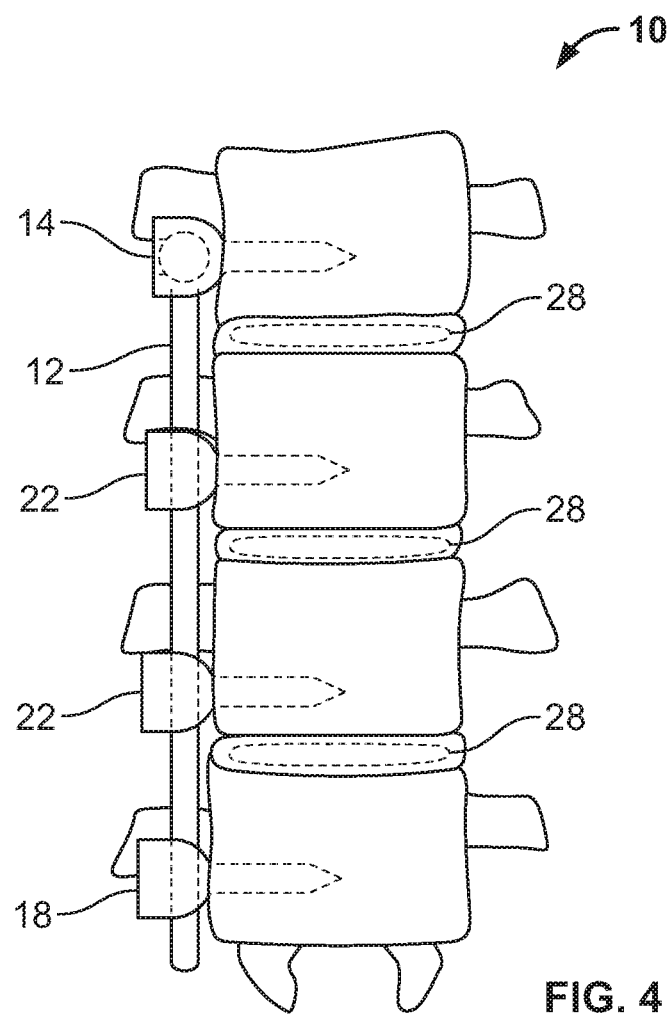
FIG. 4 is an anterior view of a multi-level spinal alignment system according to another embodiment of the present invention.
Figure 5:
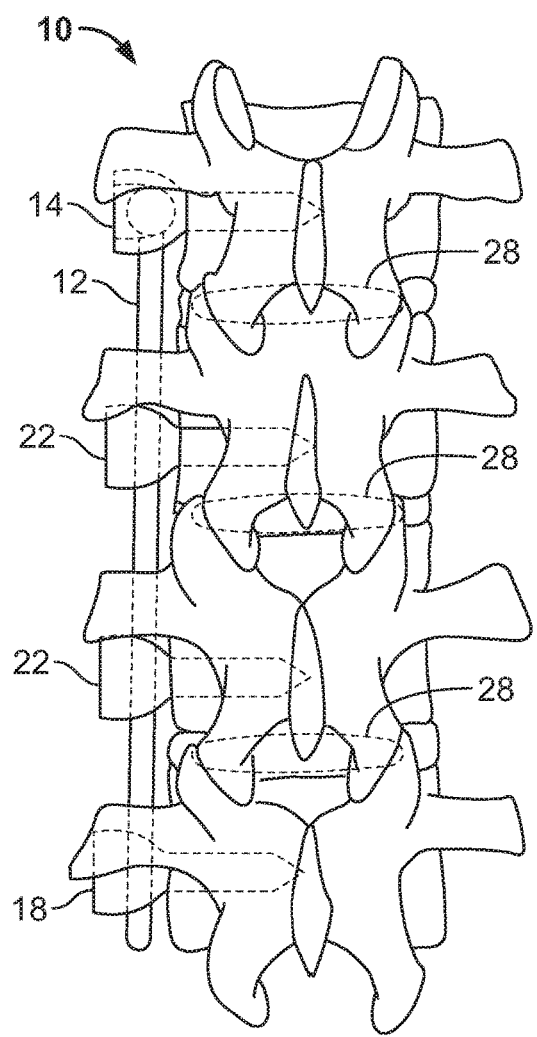
FIG. 5 is a posterior view of the multi-level spinal alignment system according to the embodiment drawn in FIG. 4.
Figure 6:
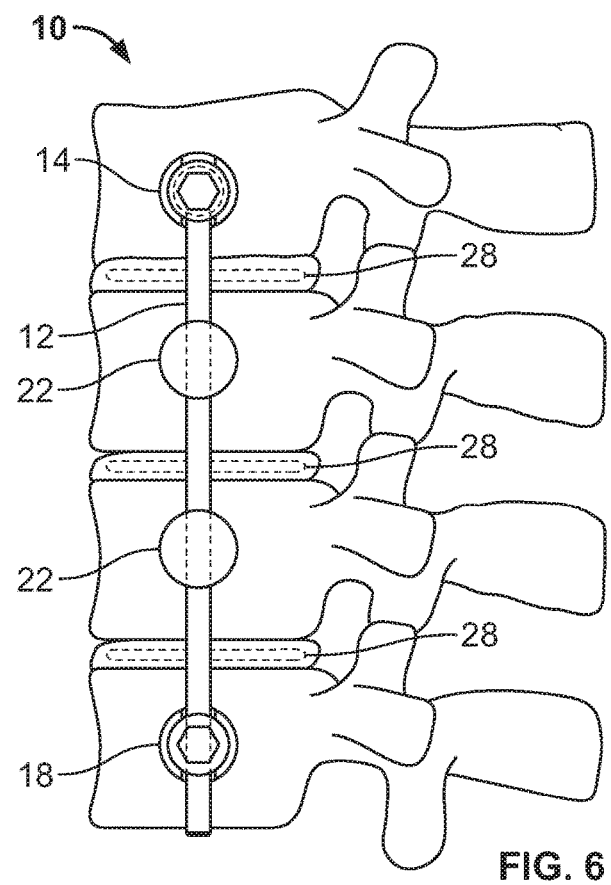
FIG. 6 is a lateral view of the multi level spinal alignment system according to the embodiment drawn in FIG. 4.

FIGS. 4-6 are anterior, posterior, and lateral views (respectively) of a multi-level spinal alignment system 10 according to another broad aspect of the present invention. In addition to the components of the single level embodiment of FIGS. 2-3 (which need not be repeated) the multi level spinal alignment system 10 includes at least one middle bone screw 22 and at least two spinal fusion implants 28, which may also preferably be introduced into the patient in a generally lateral manner (via open or minimally invasive techniques). As will be described with greater detail below, the multi-level spinal alignment system 10 of the present invention may be used to treat spinal deformities, including but not limited to scoliosis. According to one aspect of the present invention, a plurality of spinal fusion implants 28 are introduced into targeted intervertebral spaces after access has been achieved. A superior bone screw 14 is introduced into the vertebral body immediately superior to the highest of the spinal fusion implants 28. An inferior bone screw 18 is introduced into the vertebral body immediately inferior to the lowest of the spinal fusion implants 28. A middle bone screw 22 is introduced into each vertebral body in between the superior bone screw 14 and the inferior bone screw 18. As will be appreciated, the screws 14, 18, 22 and implants 28 may be introduced in any order without departing from the scope of the invention.

According to one embodiment, the cable 12 may be threaded or otherwise passed through apertures in the middle screws 22, and thereafter locked to the superior bone screw. The cable may then be pulled or otherwise manipulated such that the distance between the superior bone screw 14, the inferior bone screw 18, and any middle bone screws 22 is reduced. This serves to move the superior vertebral body, the inferior vertebral body, and any intermediate vertebral bodies so as to correct or minimize the spinal deformity. After this reduction, the cable 12 may be locked to the middle bone screws 22 and inferior bone screw 18 to maintain the superior vertebral body, inferior vertebral body, and any intermediate vertebral bodies in the resulting configuration. In addition to manner described above, it is also contemplated that the cable 12 may be coupled to the superior bone screw 14 prior to introducing the middle bone screws 22 and/or the inferior bone screw 18.

Whether in the single level or multi level embodiments, the bone screws, cable, and fusion implants of the present invention may be provided in any number of suitable manners without departing from the scope of the present invention. For example, with reference to FIG. 7, the bone screws 14, 18, 22 may each be provided having a "tulip style" cable housing 50 coupled to a shaft 52. The cable housing 50 may be integrally formed with the shaft 52 (forming a so-called "fixed axis" screw) or adjustably coupled to the shaft 52 (forming a so-called "poly-axial" screw). Any number of suitable closure mechanisms may be employed to secure the cable 12 to the respective screws 14, 18, 22, including but not limited to the threaded set screws 54. The set screws 54 include an external thread 56 dimensioned to engage within a threaded region 60 provided within each cable housing 50. The shaft 52 includes an externally disposed thread 62, which may be provided having any number of suitable pitches, lengths, widths, etc., depending upon the surgical application and patient anatomy. Other fasteners or anchors may also be used, such as those commonly used in surgical fixation procedures. The bone screws 14, 18, 22 may be cannulated in order to allow precise insertion with the use of a K-wire or other surgical insertion-facilitating device that may be commonly used in such a procedure.

The cable 12 is an elongated flexible member with a first end, a second end, and a head member 30 located at the first end, and a main portion 32 extending from the head member 30 to the second end. The head member 30 of the cable 12 may be a spherical body shaped to be received within and locked into the cable housing 50 of the superior bone screw 14. It should also be noted that the head member 30 may also be dimensioned in any number of suitable shapes necessary to facilitate surgical fixation, including but not limited to spherical, oval, flat, or rectangular depending upon the configuration of the cable housing 50. The main portion 32 may be composed of any substantially and suitable flexible material capable of performing spinal alignment including, but not limited to, steel, nylon, plastics, or various composites. Accordingly, any suitable shape for the cable 12 is useable, whether cylindrical, flat, square, or other suitable shapes and configurations within the scope of the present invention. As is described in detail below, the cable 12 is used to straighten curvature in the spine. It is also within the scope of the present invention that the cable 12 may be substituted for a rigid rod with or without a spherical head.

Figures 7, 8:
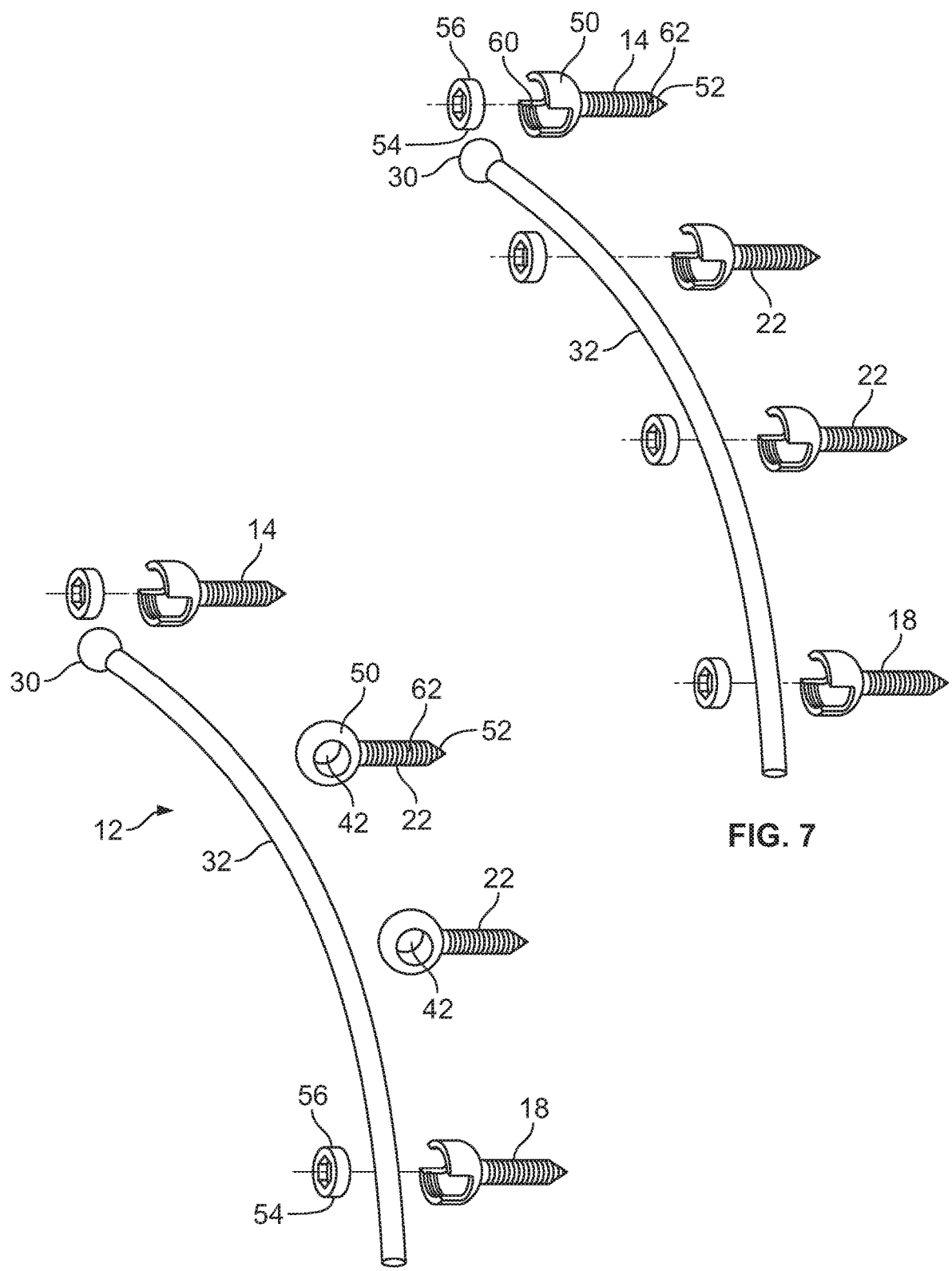
FIG. 7 is a perspective view of a multi-level spinal alignment system according to one embodiment of the present invention.
FIG. 8 is a perspective view of a multi-level spinal alignment system according to another embodiment of the present invention.

FIG. 8 illustrates a still further embodiment of the spinal alignment system 10 of the present invention, wherein the middle screws 22 include a "side-loading" cable housing 50 coupled to the shaft 52. As with the embodiment of FIG. 7, the cable housing 50 may be either integrally formed with the shaft 52 (forming a so-called "fixed axis" screw) or adjustably coupled to the shaft 52 (forming a so-called "poly-axial" screw). In either event, the cable housing 50 of each middle screw 22 includes an aperture 42 extending generally perpendicularly therethrough and dimensioned to receive the main portion 32 of the cable 12. While shown as generally circular in cross section, the aperture 42 may be provided having any number of suitable cross sectional shapes, such as an oval and/or rectangular, depending upon the cross sectional shape of the main section 32 of the cable 12.

In use, the main portion 32 of the cable 12 may be fed or otherwise directed through each aperture 42 (either before or after the head 30 of the cable 12 is locked to the superior bone screw 14). As will be discussed in greater detail below, the aperture 42 of each cable housing 50 is dimensioned such that the main portion 32 will be allowed to traverse therethrough as the spinal alignment system 10 of the present invention is tightened or adjusted to effectuate spinal deformity correction. Once such a correction has been accomplished, the set screw 54 of the inferior screw 18 may be employed to lock the spinal alignment system 10 and thereby maintain the correction.

Figure 9:
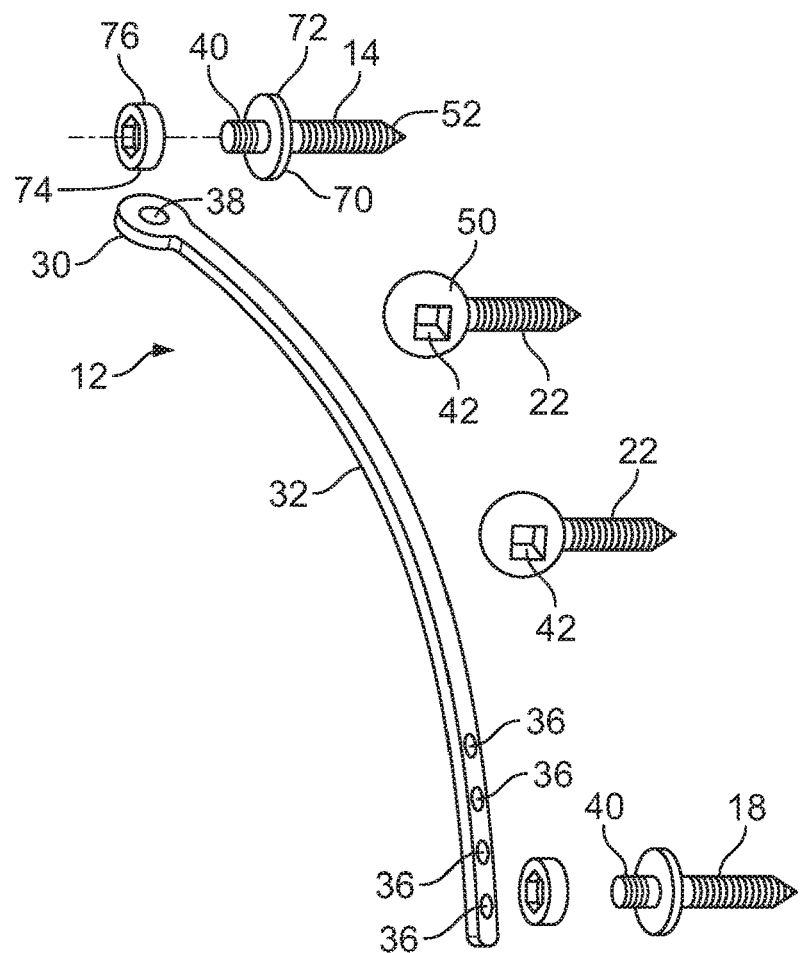
FIG. 9 is a perspective view of a multi level spinal alignment system according to yet another embodiment of the present invention.

FIG. 9 illustrates yet another embodiment of the spinal alignment system 10 of the present invention, wherein the superior and inferior bone screws 14, 18 each have a top-loading "post style" head region 70 (including a threaded post 40 and a ring member 72) coupled to the shaft 52. As with the embodiment of FIGS. 7 and 8, the head region 70 may be either integrally formed with the shaft 52 (forming a so-called "fixed axis" screw) or adjustably coupled to the shaft 52 (forming a so-called "poly-axial" screw). In either event, the threaded post 40 of the superior bone screw 14 is dimensioned to be coupled to a corresponding aperture 38 formed in the head 30 of the cable 12 shown in FIG. 9 (which represents an alternate embodiment relative to that shown in FIGS. 2-8 and which will be described in greater detail below). The threaded post 40 of the inferior bone screw 18 is dimensioned to be coupled to one of several corresponding apertures 36 formed in the main portion 32 according to the alternate embodiment of the cable 12 shown in FIG. 9. The cable housing 50 of each middle screw 22 includes an aperture 42 dimensioned to pass the main portion 32 of the cable 12 therethrough in generally the same manner as the embodiment shown in FIG. 8. Any number of suitable closure mechanisms may be employed to secure the cable 12 to the respective threaded post 40, including but not limited to the threaded nuts 74. The threaded nuts 74 include an internal thread 76 dimensioned to engage with a threaded region provided on each threaded post 40.

Figure 10:
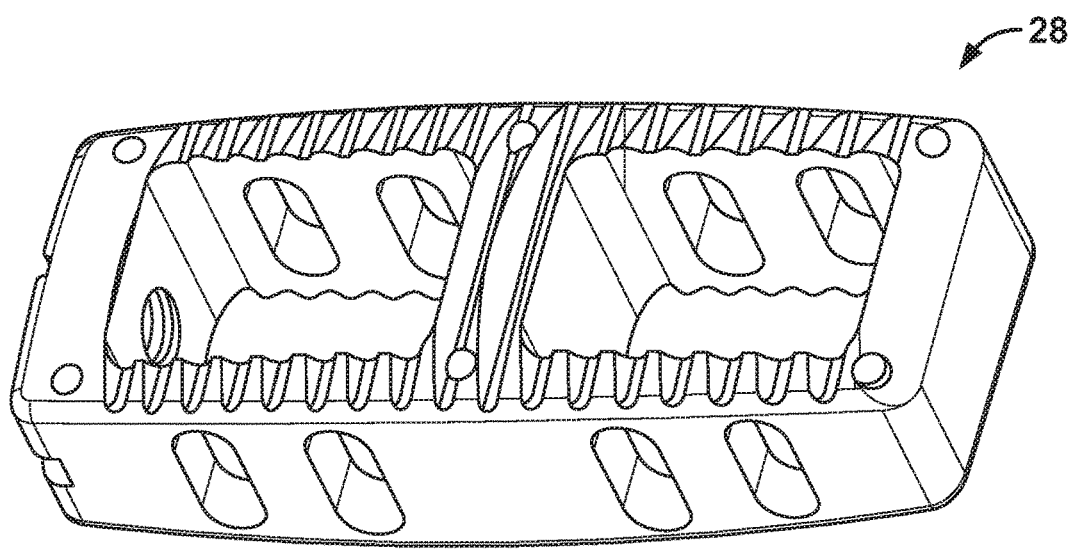
FIG. 10 is a perspective view of a spinal fusion implant according to one embodiment of the present invention.

FIG. 10 illustrates the spinal fusion implants 28 according to one embodiment of the present invention. The non-bone construction of the spinal fusion implant 28 may be provided in any number of suitable shapes and sizes depending upon the particular surgical need. The spinal fusion implant 28 may be dimensioned for use in the cervical and/or lumbar spine in any variety of ways, such as the design described in commonly owned and co-pending U.S. patent application Ser. No. 11/093,409, the entire contents of which are hereby expressly incorporated by reference into this disclosure as if set forth fully herein.

Figure 11:
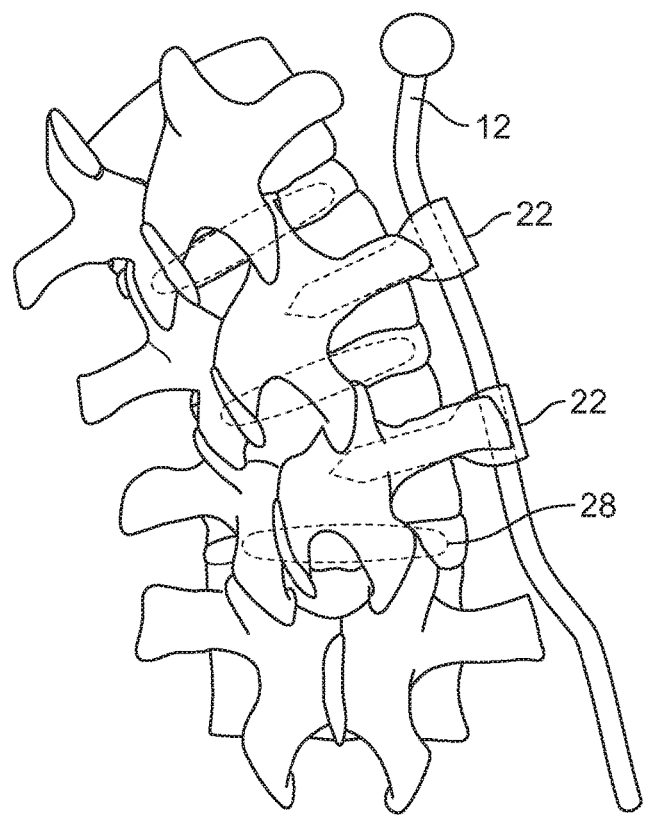
FIG. 11 illustrates aspects of performing multi-level spinal deformity correction according to one embodiment of the present invention.
Figure 12:
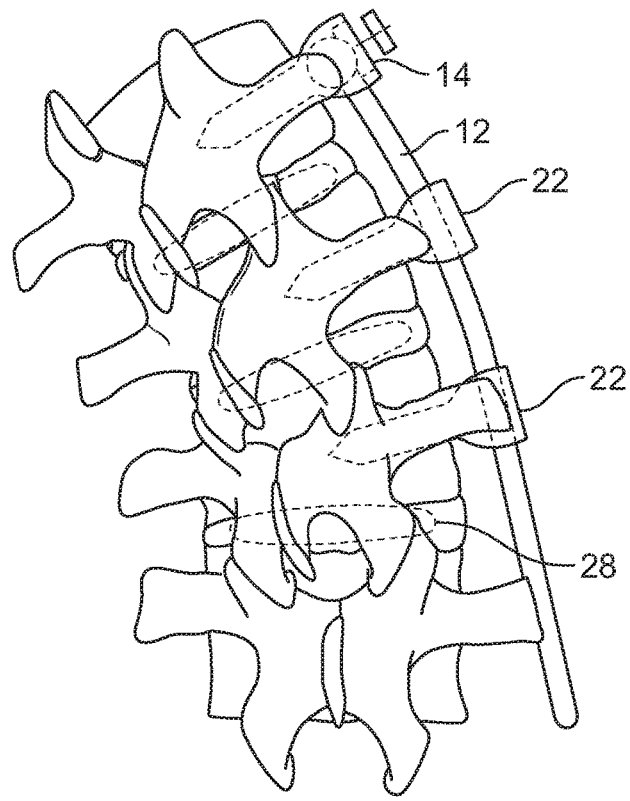
FIG. 12 illustrates aspects of performing multi-level spinal deformity correction according to another embodiment of the present invention.
Figure 13:
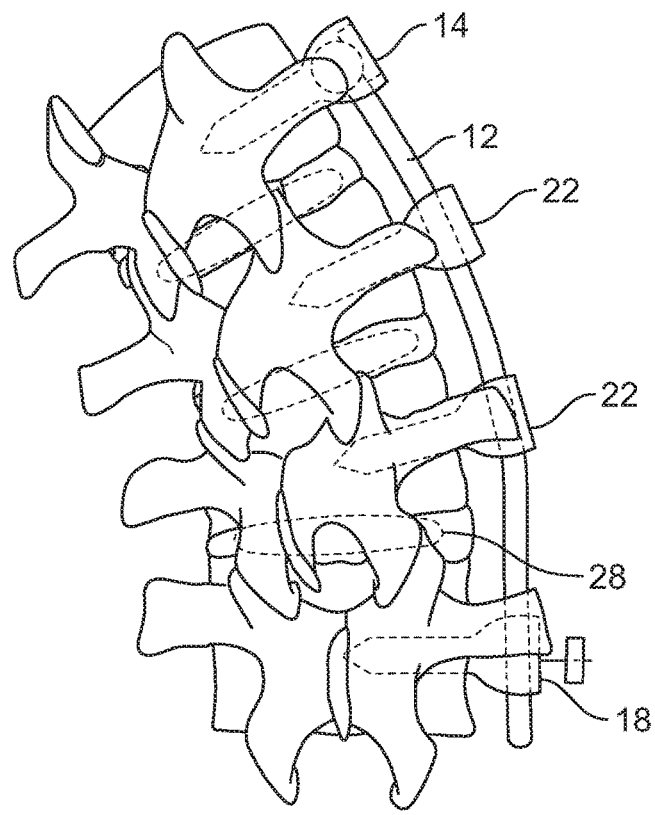
FIG. 13 illustrates aspects of performing multi-level spinal deformity correction according to yet another embodiment of the present invention.

The spinal alignment system 10 of the present invention may be employed using any number of suitable methods in addition to those previously described. FIGS. 11-13 illustrate, by way of example only, one such method of installation of the multi level spinal alignment system 10 of the present invention. In order to use the spinal alignment system 10 of the present invention in a treatment of degenerative scoliosis, a clinician must first designate the appropriate spinal fusion implant size 28. A clinician can utilize the spinal alignment system 10 in either an open or minimally invasive technique involving a generally lateral approach. In either type of procedure, a working channel must be created in a patient that reaches a targeted spinal level. According to the present invention, the preferred approach for creating this working channel is from the lateral direction (as opposed to posterior, postero-lateral or anterior approaches). After the creation of the working channel, the intervertebral space is prepared as desired, including but not limited to the use of a device for decorticating the endplates to promote fusion. After disc space preparation, the spinal fusion implants 28 may then be introduced into the prepared intervertebral spaces.

As shown in FIG. 11, once the spinal fusion implants 28 are in place, the middle bone screw(s) 22 are secured to the targeted vertebral site. The middle bone screw(s) 22 are inserted into a patient through the surgical corridor such the middle bone screw(s) are attached into intermediate vertebral bodies. Once positioned as such, the cable 12 is either passed through apertures in the middle bone screw(s) 22 or loaded into the middle bone screw(s) 22. The step of securing middle bone screw(s) 22 to a vertebral body may be omitted depending on whether a single level or multi level system is being used. The use of middle bone screw(s) 22 is not necessary in a single level spinal alignment system.

FIG. 12 illustrates a second step involving the insertion of the superior bone screw 14. According to one embodiment of the present invention, the superior bone screw 14 is inserted into a patient through a surgical corridor such that the superior bone screw 14 is attached into the vertebral body immediately superior to the highest of the spinal fusion implants 28. Once positioned as such, the head member 30 of the cable 12 is loaded into the superior bone screw 14 and locked into position.

FIG. 13 illustrates a third step involving the insertion of the inferior bone screw 18. According to one embodiment of the present invention, the inferior bone screw 18 is inserted into a patient through a surgical corridor such that the inferior bone screw 18 is attached into the vertebral body immediately inferior to the lowest of the spinal fusion implants 28. Once positioned as such, the cable 12 may then be pulled or otherwise manipulated such that the distance between the superior bone screw 14, the inferior bone screw 18, and any middle bone screw(s) 22 is reduced. This serves to move the superior vertebral body, the inferior vertebral body, and any intermediate vertebral bodies so as to correct or minimize the spinal deformity. After this reduction, the main portion 32 of the cable 12 may be loaded and locked into inferior bone screw 18. Consequently, the inferior bone screw 18 maintains the superior vertebral body, inferior vertebral body, and any intermediate vertebral bodies in compression.

Figure 14:
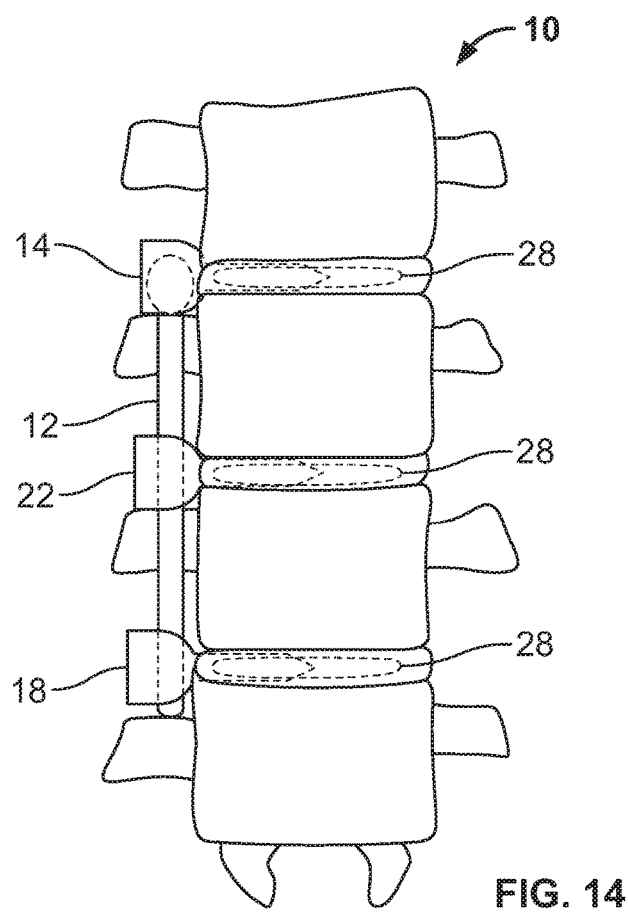
FIG. 14 is an anterior view illustrating a spinal alignment system according to an alternate embodiment of the present invention.
Figure 15:
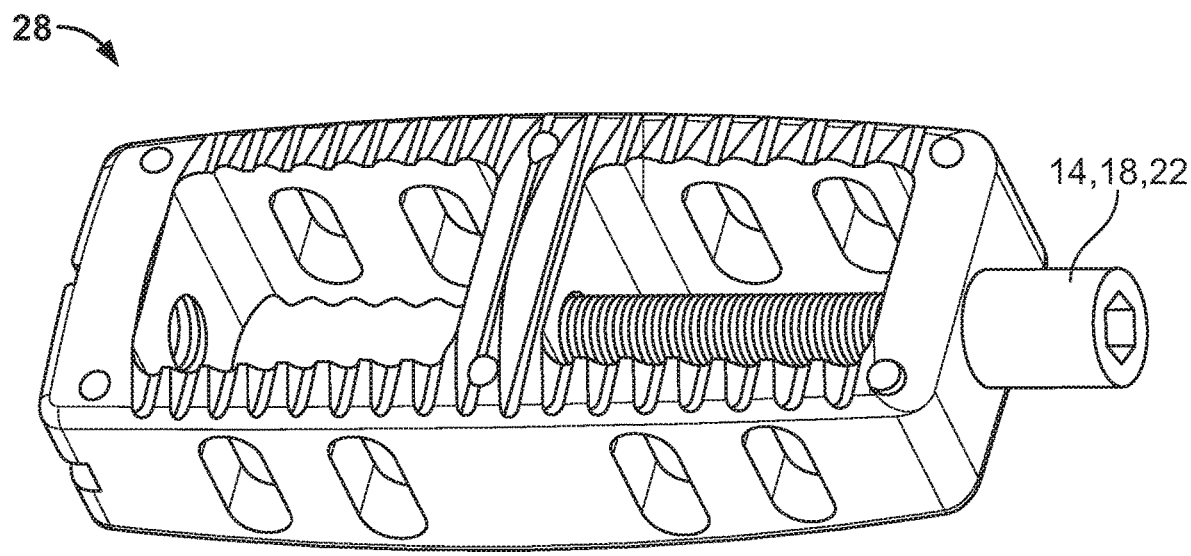
FIGS. 15-16 are perspective views of the spinal fusion implant of FIG. 14 with a bone screw extending partially through the implant (FIG. 15) and substantially through the entire implant (FIG. 16) according to the present invention.
Figure 16:
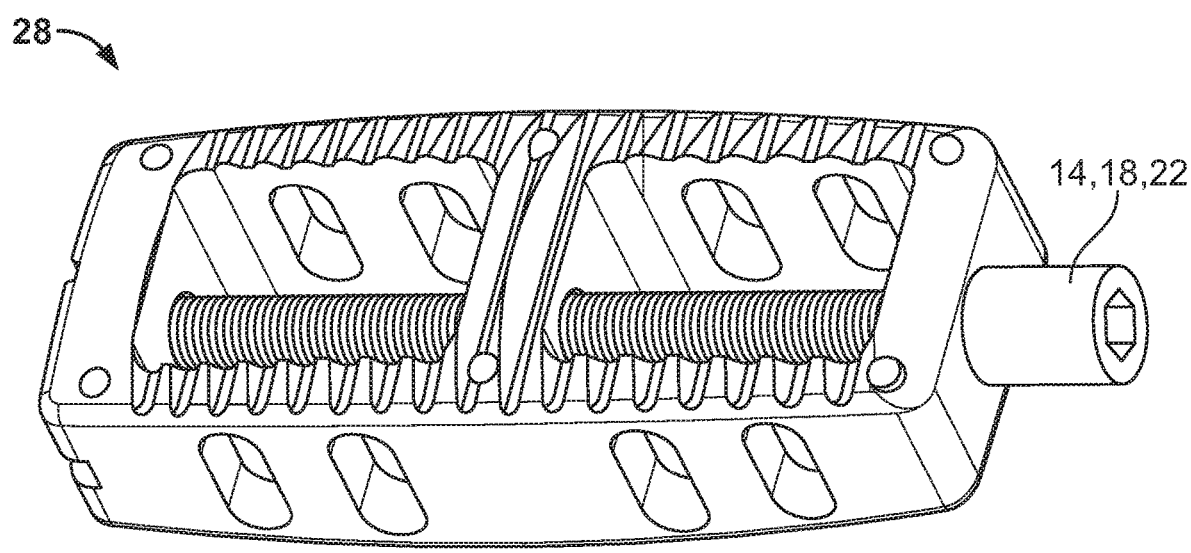

FIGS. 14-16 illustrates another exemplary embodiment of the present invention, wherein the spinal alignment system 10 is configured such that the superior bone screws 14, inferior bone screws 18, and/or middle bone screw(s) 22 may be secured directly into a spinal fusion implant 28 instead of being secured into the vertebral bodies. The bone screws (superior 14, inferior 18 or middle bone screw(s) 22) may be introduced into the implants 28 before, during and/or after the implants 28 are introduced into the respective intervertebral spaces. As shown in FIGS. 15-16, a bone screw (superior 14, inferior 18 or middle bone screw(s) 22) may be received into a spinal fusion implant 28 by either securing the bone screw substantially midway through the implant 28 (FIG. 15) or substantially through the entire implant 28 (FIG. 16). The cable 12 is coupled to the bone screws and is then capable of being pulled or otherwise manipulated to move the spinal implants 28 towards one another and thereby effect spinal deformity correction.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A method of treating spinal deformities, comprising the steps of:
   accessing an intervertebral space forming part of a spinal deformity via a generally lateral approach;
   introducing a spinal fusion implant into said intervertebral space via a generally lateral approach;
   introducing first and second bone screws into first and second vertebral bodies via a generally lateral approach; and
   coupling an elongate member to said first and second bone screws to minimize said spinal deformity comprising:
      receiving a head member of the elongate member at said first bone screw and locking said head member of the elongate member to said first bone screw, wherein said head member contacts the first bone screw directly, the head member having a different cross-section from a body portion of the elongate member; and
      coupling the body portion of the elongate member to the second bone screw, wherein the elongate member starts from the head member and extends to an end of the body portion.

2. The method of treating spinal deformities of claim 1, wherein the step of accessing the intervertebral space is performed using a minimally invasive technique.

3. The method of treating spinal deformities of claim 1, wherein said step of coupling an elongate member includes manipulating said elongate member such that the distance between said first and second screws is reduced.

4. A method for treating spinal deformities, comprising:
   accessing a target intervertebral space of a patient via a generally lateral approach;
   introducing a spinal fusion implant into the target intervertebral space;
   placing a first bone screw in a first vertebral body of the patient;
   placing a second bone screw in a second vertebral body of the patient;
   receiving a head member of the flexible elongate member at said first bone screw and locking said head member of a flexible elongate member to the first bone screw, wherein said head member contacts the first bone screw directly, the head member having a different cross-section from a body portion of the flexible elongate member; and
   securing the body portion of the flexible elongate member to the second bone screw, the flexible elongate member configured to maintain a fixed distance between the first bone screw and the second bone screw and improve a spinal deformity, wherein the elongate member starts from the head member and extends to an end of the body portion.

5. The method of claim 4, comprising the step: placing a second spinal fusion implant into a second targeted intervertebral space of the patient.

6. The method of claim 5, comprising the step: placing a third bone screw in a third vertebral body of the patient.

7. The method of claim 6, comprising the step: securing the flexible elongate member to the third bone screw.

8. The method of claim 4, the flexible elongate member comprising a cable.

9. The method of claim 4, wherein said first and second bone screws each includes a housing comprising a threaded post and ring member, and wherein the head member comprises an aperture coupleable to the threaded post.

10. The method of claim 9, comprising the step securing the flexible elongate member to the housing using a set screw.

11. The method of claim 4, wherein said at least one of said first screw, said second screw, and said third screw includes a side-loading housing having an aperture dimensioned to receive said elongate member.

12. The method of claim 4, wherein the spinal deformity comprises scoliosis.

13. The method of claim 4, wherein said step of receiving the head member at said first bone screw and locking said head member of the elongate member to said first bone screw comprises placing the head member completely within a housing of the first bone screw or coupling an aperture in the head portion to a post of the first bone screw.

14. A method for treating scoliosis, comprising:
   accessing a target intervertebral space of a patient via a generally lateral approach;
   introducing a spinal fusion implant into the target intervertebral space;
   placing a first bone screw in a first vertebral body of the patient;
   placing a second bone screw in a second vertebral body of the patient;
   receiving a head member of the flexible elongate member at said first bone screw and locking said head member of a flexible elongate member to the first bone screw, wherein said head member contacts the first bone screw directly, the head member having a different cross-section from a body portion of the flexible elongate member; and
   securing the body portion of the flexible elongate member to the second bone screw, the flexible elongate member configured to maintain a fixed distance between the first bone screw and the second bone screw and reduce curvature of a spine of the patient, wherein the elongate member extends from the head member to an end of the body portion.

15. The method of claim 14, comprising the step: placing a second spinal fusion implant into a second targeted intervertebral space of the patient.

16. The method of claim 15, comprising the step: placing a third bone screw in a third vertebral body of the patient.

17. The method of claim 16, comprising the step: securing the flexible elongate member to the third bone screw.

18. The method of claim 14, wherein said first and second bone screws each includes a tulip-shaped housing.

19. The method of claim 18, comprising the step securing the flexible elongate member to the tulip-shaped housing using a set screw.

20. The method of claim 14, wherein said at least one of said first screw, said second screw, and said third screw includes a side-loading housing having an aperture dimensioned to receive said elongate member.

* * * * *